United States Patent [19]

Mills et al.

[11] Patent Number: 5,387,595
[45] Date of Patent: Feb. 7, 1995

[54] ALICYCLIC COMPOUNDS AS TACHYKININ RECEPTOR ANTAGONISTS

[75] Inventors: Sander G. Mills, Woodbridge; Paul E. Finke, Milltown; Malcolm MacCoss, Freehold; Daniel J. Miller, Edison; Dennis J. Underwood, Roselle, all of N.J.

[73] Assignee: Merck & Co., Inc., Rahway, N.J.

[21] Appl. No.: 935,754

[22] Filed: Aug. 26, 1992

[51] Int. Cl.⁶ ............... C07D 213/40; C07C 235/26; C07C 275/24; C07C 57/46
[52] U.S. Cl. .................. 514/357; 514/595; 514/622; 546/332; 546/337; 564/47; 564/171
[58] Field of Search ............ 546/337, 332; 564/47, 564/171; 514/357, 595, 622

[56] References Cited

U.S. PATENT DOCUMENTS

| | | | |
|---|---|---|---|
| 3,506,673 | 4/1970 | Warawa et al. | 260/294.2 |
| 3,574,165 | 4/1971 | Braus et al. | 524/326 |
| 4,804,661 | 2/1989 | Ferrine et al. | 514/255 |
| 4,943,578 | 7/1990 | Naylor et al. | 514/242 |
| 5,064,838 | 11/1991 | Carr et al. | 514/317 |

FOREIGN PATENT DOCUMENTS

| | | | |
|---|---|---|---|
| 0142322 | 5/1985 | European Pat. Off. | 546/337 |
| 0360390 | 3/1990 | European Pat. Off. | 514/317 |
| 0436334 | 7/1991 | European Pat. Off. | 514/317 |
| 0499313 | 8/1992 | European Pat. Off. | 514/317 |
| WO90/05525 | 5/1990 | WIPO | 514/317 |
| WO90/05729 | 5/1990 | WIPO | 514/317 |
| WO92/18899 | 12/1991 | WIPO | 514/317 |
| WO92/01679 | 2/1992 | WIPO | 514/317 |
| WO92/06079 | 4/1992 | WIPO | 514/317 |
| WO92/12128 | 7/1992 | WIPO | 514/317 |
| WO92/12151 | 7/1992 | WIPO | 514/317 |
| WO92/12152 | 7/1992 | WIPO | 514/317 |
| WO92/15585 | 9/1992 | WIPO | 514/317 |

OTHER PUBLICATIONS

J. Clin. Invest., 74, 1532–1539 (1984), Payan, et al.
Life Sci., 49, 1941–1953 (1991), Frossard, et al.
Life Sci., 50, PL-101-PL-106(1992), Emonds-Alt, et al.
J. Med. Chem. 35, 2591–2600 (1992), Lowe, et al.
Biochem. & Biophys. Res. Comm., 184(3), 1418–1424 (1992), Advenier, et al.
Biorg. & Med. Chem. Lett., 2(1), 37–40 (1992), Peyronel et al.
Biorg. & Med. Chem. Lett., 2(6), 559–64 (1992), Howson, et al.
Drug New Perspect., 5(4) 223–228 (1992), Lowe, et al.

Primary Examiner—C. Warren Ivy
Assistant Examiner—Zinna N. Davis
Attorney, Agent, or Firm—J. Eric Thies; David L. Rose

[57] ABSTRACT

Substituted alicyclic compounds of the general structural formula:

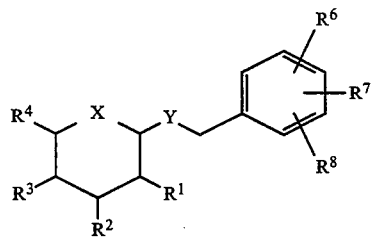

are tachykinin receptor antagonists useful in the treatment of inflammatory diseases, pain or migraine, and asthma.

8 Claims, No Drawings

ALICYCLIC COMPOUNDS AS TACHYKININ RECEPTOR ANTAGONISTS

SUMMARY OF THE INVENTION

This invention is concerned with novel compounds represented by structural formula I:

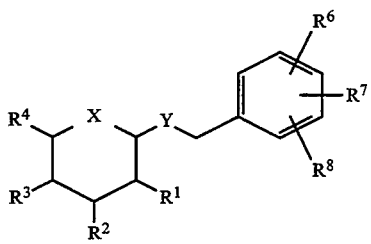

wherein $R^1$, $R^2$, $R^3$, $R^4$, $R^6$, $R^7$, $R^8$, X and Y are hereinafter defined.

The invention is also concerned with processes to prepare the instant compounds, pharmaceutical formulations with these compounds as active ingredients and the use of these compounds and their formulations in the treatment of certain disorders.

The compounds of this invention are tachykinin receptor antagonists and are useful in the treatment of inflammatory diseases, pain or migraine and asthma.

BACKGROUND OF THE INVENTION

Analgesia has historically been achieved in the central nervous system by opiates and analogs which are addictive, and peripherally by cyclooxygenase inhibitors that have gastric side effects. Substance P antagonists induce analgesia both centrally and peripherally. In addition, substance P antagonists are inhibitory of neurogenic inflammation.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, Pharmacol, Rev., 1983, 35, 85–141). The NK1 and NK2 receptor subtypes are implicated in synaptic transmission (Laneuville et al., Life Sci., 42:1295–1305 (1988)).

The receptor for substance P is a member of the superfamily of G protein-coupled receptors. This superfamily is an extremely diverse group of receptors in terms of activating ligands and biological functions. In addition to the tachykinin receptors, this receptor superfamily includes the opsins, the adrenergic receptors, the muscarinic receptors, the dopamine receptors, the serotonin receptors, a thyroid-stimulating hormone receptor, a luteinizing hormone-choriogonadotropic hormone receptor, the product of the oncogene ras, the yeast mating factor receptors, a Dictyostelium cAMP receptor, and receptors for other hormones and neurotransmitters (see A. D. Hershey, et al., J. Biol. Chem., 1991, 226, 4366–4373).

Substance P (also called "SP" herein) is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence Phe-X-Gly-Leu-Met-$NH_2$. In addition to SP the known mammalian tachykinins include neurokinin A and neurokinin B. The current nonmenclature designates the receptors for SP, neurokinin A, and neurokinin B as NK-1, NK-2, and NK-3, respectively.

More specifically, substance P is a pharmacologically-active neuropeptide that is produced in mammals and possesses a characteristic amino acid sequence that is illustrated below:

Arg-Pro-Lys-Pro-Gln-Gln-Phe-Phe-Gly-Leu-Met-$NH_2$ (Chang et al., Nature New Biol. 232, 86 (1971); D. F. Veber et al., U.S. Pat. No. 4,680,283).

Neurokinin A possesses the following amino acid sequence:

His-Lys-Thr-Asp-Ser-Phe-Val-Gly-Leu-Met-$NH_2$.

Neurokinin B possesses the following amino acid sequence:

Asp-Met-His-Asp-Phe-Phe-Val-Gly-Leu-Met-$NH_2$.

Substance P acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., Science., 199, 1359 (1978); P. Oehme et al., (Science, 208,305 (1980)) and plays a role in sensory transmission and pain perception (T. M. Jessell, Advan. Biochem. Psychopharmacol. 28, 189 (1981)). For-example, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (Dec. 1987) 8 506–510]. In particular, substance P has been shown to be involved in the transmission of pain in migraine (see B. E. B. Sandberg et al., Journal of Medicinal Chemistry, 25, 1009 (1982)), and in arthritis (Levine et al. Science, (1984) 226 547–549). These peptides-have also been implicated in gastrointestinal (GI) disorders and diseases of the GI tract, such as inflammatory bowel disease, ulcerative colitis and Crohn's disease, etc. (see Mantyh et al., Neuroscience, 25 (3), 817–37 (1988) and D. Regoli in "Trends in Cluster Headache" Ed. F. Sicuteri et al., Elsevier Scientific Publishers, Amsterdam, 1987, pp. 85–95).

It is also hypothesized that there is a neurogenic mechanism for arthritis in which substance P may play a role (Kidd et al., "A Neurogenic Mechanism for Symmetric Arthritis" in The Lancet, 11 November 1989 and Gronblad et al., "Neuropeptides in Synovium of Patients with Rheumatoid Arthritis and Osteoarthritis" in J. Rheumatol. (1988) 15(12) 1807–10). Therefore, substance P is believed to be involved in the inflammatory response in diseases such as rheumatoid arthritis and osteoarthritis (O—Byrne etal., in Arthritis and Rheumatism (1990) 33 1023-8). Other disease areas where tachykinin antagonists are believed to be useful are allergic conditions (Hamelet et al., Can. J. Pharmacol. Physiol. (1988) 66 1361-7), immunoregulation (Lotz et al., Science (1988) 241 1218–21, Kimball et al., J. Immunol. (1988) 141 (10) 3564–9 and A. Perianin, et al., Biochem. Biophys. Res. Commun. 161, 520 (1989)) vasodilation, bronchospasm, reflex or neuronal control of the viscera (Mantyh et al., PNAS (1988) 3235-9) and, possibly by arresting or slowing β-amyloid-mediated neurodegenerative changes (Yankner et al., Science, (1990) 25Q, 279-82) in senile dementia of the Alzheimer type, Alzheimer's disease and Downs Syndrome.

Substance P may also play a role in demyelinating diseases such as multiple sclerosis and amyotrophic lateral sclerosis [J. Luber-Narod et. al., poster to be presented at C.I.N.P. XVIIIth Congress, 28th June-2nd July, 1992, in press], and in disorders of bladder function such as bladder detrusor hyper-reflexia (Lancet, 16th May, 1992, 1239). Antagonists selective for the substance P and/or the neurokinin A receptor may be useful in the treatment of asthmatic disease (Frossard et al., Life Sci., 49, 1941–1953 (1991); Advenier, et al., Biochem. Biophys. Res. Comm., ! 84(3), 1418–1424 (1992)).

It has furthermore been suggested that tachykinins have utility in the following disorders: depression; dysthymic disorders; chronic obstructive airways disease; hypersensitivity disorders such as poison ivy; vasospastic diseases such as angina and Reynauld's disease; fibrosing and collagen diseases such as scleroderma and eosinophillic fascioliasis; reflex sympathetic dystrophy such as shoulder/hand syndrome; addiction disorders such as alcoholism; stress related somatic disorders; neuropathy; neuralgia; disorders related to immune enhancement or suppression such as systemic lupus erythmatosis (EPO Publication No. 0,436,334); ophthalmic diseases such as conjunctivitis, vernal conjunctivitis, and the like; and cutaneous diseases such as contact dermatitis, atropic dermatitis, urticaria, and other eczematoid dermatitis (EPO Publication No. 0,394,989).

In the recent past, some attempts have been made to provide peptide-like substances that are antagonists for substance P and other tachykinin peptides in order to more effectively treat the various disorders and diseases listed above. See for example European patent applications (EPO Publication Nos. 0,347,802, 0,401,177 and 0,412,452) which disclose various peptides as neurokinin A antagonists. Similarly, EPO Publication No. 0,336,230 discloses heptapeptides which are substance P antagonists useful in the treatment of asthma. Merck U.S. Pat. No. 4,680,283 also discloses peptidal analogs of substance P.

Certain inhibitors of tachykinins have been described in U.S. Pat. No. 4,501,733, by replacing residues in substance P sequence by Trp residues.

A further class of tachykinin receptor antagonists, comprising a monomeric or dimeric hexa- or heptapeptide unit in linear or cyclic form, is described in GB-A-2216529.

The peptide-like nature of such substances make them too labile from a metabolic point of view to serve as practical therapeutic agents in the treatment of disease. The non-peptidic antagonists of the present invention, on the other hand, do not possess this drawback, as they are expected to be more stable from a metabolic point of view than the previously-discussed agents.

It is known in the art that baclofen (β-(aminoethyl)-4-chlorobenzenepropanoic acid) in the central nervous system effectively blocks the excitatory activity of substance P, but because in many areas the excitatory responses to other compounds such as acetylcholine and glutamate are inhibited as well, baclofen is not considered a specific substance P antagonist. Pfizer WIPO patent applications (PCT Publication NOS. WO 90/05525 and WO 90/05729) and publications (Science, 251, 435–437 (1991); Science, 251, 437–439 (1991)) disclose 2-arylmethyl-3-substituted amino-quinuclidine derivatives which are disclosed as being useful as substance P antagonists for treating gastrointestinal disorders, central nervous system disorders, inflammatory diseases and pain or migraine. A Glaxo European patent application (EPO Publication No. 0,360,390) discloses various spirolactam-substituted amino acids and peptides which are antagonists or agonists of substance P. A Pfizer WIPO patent application (PCT Publication No. WO 92/06079) discloses fused-ring analogs of nitrogen-containing nonaromatic heterocycles as useful for the treatment of diseases mediated by an excess of substance P. A Sanofi publication (Life Sci., 50, PL101-PL106 (1992)) discloses a 4-phenyl piperidine derivative as an antagonist of the neurokinin A (NK2) receptor.

DETAILED DESCRIPTION OF THE INVENTION

The novel compound of this invention is represented by structural formula I:

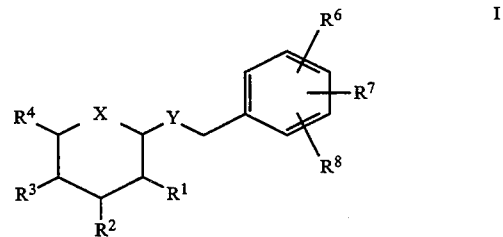

or a pharmaceutically acceptable salt thereof, wherein:
$R^1$ is selected from the group consisting of:
(1) phenyl, unsubstituted or substituted with one or more of $R^{11}$, $R^{12}$ and $R^{13}$, wherein $R^{11}$, $R^{12}$ and $R^{13}$ are as defined below;
(2) $C_{1-8}$ alkyl, unsubstituted or substituted with one or more of the substituents selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$NR^9R^{10}$, wherein $R^9$ and $R^{10}$ are independently selected from:
    (i) hydrogen,
    (ii) phenyl,
    (iii) $C_{1-6}$ alkyl, unsubstituted or substituted with one or more of the substituents selected from:
      (A) hydroxy,
      (B) oxo,
      (C) $C_{1-6}$ alkoxy,
      (D) phenyl-$C_{1-3}$ alkoxy,
      (E) phenyl,
      (F) —CN,
      (G) halo,
      (H) $NR^{14}R^{15}$, wherein $R^{14}$ and $R^{15}$ are independently selected from hydrogen, $C_{1-6}$ alkyl, and phenyl,
      (I) -heteroaryl, wherein heteroaryl is selected from the group consisting of:
        (a) furanyl,
        (b) pyrrolyl,
        (c) pyridyl,
        (d) imidazolyl, (e) oxadiazolyl,
(f) pyrazolyl,
(g) triazolo,
(h) tetrazolo,
(i) pyrimidyl,
(j) oxazolo,
(k) isooxazolo,
(l) thiazolo, and
(m) thiadiazolo, and wherein the heteroaryl is unsubstituted or substituted with one or more substituent(s) selected from:
(I) $C_{1-6}$ alkyl,
(II) $C_{1-6}$ alkoxy,
(III) —$NR^{14}R^{15}$, wherein $R^{14}$ and $R^{15}$ are as defined above,
(IV) halo, and
(V) trifluoromethyl;
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$NR^{14}CONR^9R^{10}$, wherein $R^9$, $R^{10}$ and $R^{14}$ are as defined above,
(l) —$CONR^9R^{10}$, wherein $R^9$ and $R^{10}$ are as defined above,
(m) —$COR^9$, wherein $R^9$ is as defined above,
(n) $CO_2R^9$, wherein $R^9$ is as defined above,
(o) —$S(O)_n$-$R^9$, wherein n and $R^9$ are as defined above;
(3) —$R^9$, wherein $R^9$ is as defined above, with the proviso that $R^9$ is other than hydrogen or phenyl;
$R^2$ is independently selected from the group consisting of:
(1) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR_9CO^2R^{10}$, wherein $R^9$ and $R^{10}$ are as defined above,
(k) —$NR_{14}CONR^9R^{10}$, wherein $R^9$, $R^{10}$ and $R^{14}$ are as defined above,
(l) —$CONR^9R^{10}$, wherein $R^9$ and $R^{10}$ are as defined above,
(m) —$COR^9$, wherein $R^9$ is as defined above,
(n) —$CO_2R^9$, wherein $R^9$ is as defined above,
(o) —$S(O)_n$—$R^9$, wherein n is 0, 1 or 2 and $R^9$ is as defined above; and
(2) —$R^9$, wherein $R^9$ is as defined above, with the proviso that $R^9$ is other than hydrogen or phenyl;
$R^3$ and $R^4$ are independently selected from the group consisting of
(1) hydrogen;
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$NR^{14}CONR^9R^{10}$, wherein $R^9$, $R^{10}$ and $R^{14}$ are as defined above,
(l) —$CONR^9R^{10}$, wherein $R^9$ and $R^{10}$ are as defined above,
(m) —$COR^9$, wherein $R^9$ is as defined above,
(n) —$CO_2R^9$, wherein $R^9$ is as defined above;
(o) —$S(O)_n$—$R^9$, wherein n is 0 1 or 2 and $R^9$ is as defined above,
(3) phenyl, unsubstituted or substituted with one or more of $R^6$, $R^7$ and $R^8$, wherein $R^6$, $R^7$ and $R^8$ are as defined below; and the groups $R^3$ and $R^4$ may be joined together by a $C_{3-4}$ alkyl or a $C_{3-4}$ alkenyl to form a carbocyclic ring selected from the group consisting of:
(a) cyclopentyl,
(b) cyclohexyl,
(c) phenyl, and wherein the carbocyclic ring is unsubstituted or substituted with one or more substituents selected from:
(i) $C_{1-6}$ alkyl,
(ii) $C_{1-6}$ alkoxy,
(iii) —$NR^9R^{10}$, wherein $R^9$ and $R^{10}$ are as defined above,
(iv) halo, and
(v) trifluoromethyl;
$R^6$, $R^7$ and $R^8$ are independently selected from the group consisting of:
(1) hydrogen;
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$NR^{14}CONR^9R^{10}$, wherein $R^9$, $R^{10}$ and $R^{14}$ are as defined above,
(l) —$CONR^9R^{10}$, wherein $R^9$ and $R^{10}$ are as defined above,
(m) —$COR^9$, wherein $R^9$ is as defined above,
(n) —$CO_2R^9$, wherein $R^9$ is as defined above,
(o) —$S(O)_n$-$R^9$, wherein n is 0, 1 or 2 and $R^9$ is as defined above;
(3) $C_{2-6}$ alkenyl, unsubstituted or substituted with one or more of the substituent(s) selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo, (h) —CONR$^9$R$^{10}$ wherein R$^9$ and R$^{10}$ are as defined above,
(i) —COR$^9$ wherein R$^9$ is as defined above,
(j) —CO$_2$R$^9$, wherein R$^9$ is as defined above;
(4) C$_{2-6}$ alkynyl;
(5) phenyl, unsubstituted or substituted with one or more of the substituent(s) selected from:
(a) hydroxy,
(b) C$_{1-6}$ alkoxy,
(c) C$_{1-6}$ alkyl,
(d) C$_{2-5}$ alkenyl,
(e) halo,
(f) —CN,
(g) —NO$_2$,
(h) —CF$_3$,
(i) —(CH$_2$)$_n$-NR$^9$R$^{10}$, wherein n, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —NR$^{14}$CONR$^9$R$^{10}$, wherein R$^9$, R$^{10}$ and R$^{14}$ are as defined above,
(m) —CONR$^9$R$^{10}$, wherein R$^9$ and R$^{10}$ are as defined above,
(n) —COR$^9$, wherein R$^9$ is as defined above,
(o) —CO$_2$R$^9$, wherein R$^9$ is as defined above,
(p) —S(O)$_n$-R$^9$, wherein n is 0, 1 or 2 and R$^9$ is as defined above;
(6) halo,
(7) —CN,
(8) —CF$_3$,
(9) —OCF$_3$,
(10) —NO$_2$,
(11) hydroxy,
(12) C$_{1-6}$alkoxy,
(14) —COR$^9$, wherein R$^9$ is as defined above,
(15) —CO$_2$R$^9$, wherein R$^9$ is as defined above;
(15) —CONR$^9$COR$^{10}$, wherein R$^9$ and R$^{10}$ are as defined above,
(16) —SR$^{14}$, wherein R$^{14}$ is as defined above,
(17) —SOR$^{14}$, wherein R$^{14}$ is as defined above,
(18) —SO$_2$R$^{14}$, wherein R$^{14}$ is as defined above,
(19) —NR$^9$R$^{10}$, wherein R$^9$ and R$^{10}$ are as defined above,
(10) —NR$^9$COR$^{10}$, wherein R$^9$ and R$^{10}$ are as defined above,
(11) —NR$^9$CO$_2$R$^{10}$, wherein R$^9$ and R$^{10}$ are as defined above, and
(12) —NR$^{14}$CONR$^9$R$^{10}$, wherein R$^9$, R$^{10}$ and R$^{14}$ are as defined above;
R$^{11}$, R$^{12}$ and R$^{13}$ are independently selected from the definitions of R$^6$, R$^7$ and R$^8$;
X is (1) absent,
(2) —CH(R$^5$)—, wherein R$^5$ is independently selected from the definitions of R$^9$ and R$^{10}$, or
(3) —C$_{2-3}$ alkyl, unsubstituted or substituted with R$^5$, wherein R$^5$ is as defined above;
Y is selected from the group consisting of:
(1) —O—,
(2) —S—,
(3) —N(R$^9$)—, wherein R$^9$ is as defined above,
(4) —N(COR$^9$)—, wherein R$^9$ is as defined above,
(5) —N(CO$_2$R$^9$)—, wherein R$^9$ is as defined above, and
(6) —N(CONR$^9$R$^{10}$)—, wherein R$^9$ and R$^{10}$ are as defined above.

The compounds of the present invention have asymmetric centers and may exist both as enantiomers and diastereomers. Accordingly, the present invention includes all such isomers and mixtures thereof.

In addition compounds with carbon-carbon double bonds may occur in Z- and E- forms with all isomeric forms of the compounds being included in the present invention.

When any variable (e.g., alkyl, aryl, R$^6$, R$^7$, R$^8$, R$^9$, R$^{10}$, R$^{11}$, R$^{12}$, R$^{13}$, etc ) occurs more than one time in any variable or in Formula I, its definition on each ocurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentory. "Alkenyl" is intended to include hydrocarbon chains of a specified number of carbon atoms of either a straight- or branched- configuration and at least one unsaturation, which may occur at any point along the chain, such as ethenyl, propenyl, butenyl, pentenyl, dimethylpentyl, and the like, and includes E and Z forms, where applicable. "Halogen" or "halo", as used herein, means fluoro, chloro, bromo and iodo.

The term "aryl" means phenyl or naphthyl either unsubstituted or substituted with one, two or three substituents selected from the group consisting of halo, C$_{1-4}$-alkyl, C$_{1-4}$-alkoxy, NO$_2$, CF$_3$, C$_{1-4}$-alkylthio, OH, —N(R$^9$)$_2$, —CO$_2$R$^9$, C$_{1-4}$-perfluoroalkyl, C$_{3-6}$-perfluorocycloalkyl, and tetrazol-5-yl.

The term "heteroaryl" means an unsubstituted, monosubstituted or disubstituted five or six membered aromatic heterocycle comprising from 1 to 3 heteroatoms selected from the group consisting of O, N and S and wherein the substituents are members selected from the group consisting of —OH, —SH, —C$_{1-4}$-alkyl, —C$_{1-4}$-alkoxy, —CF$_3$, halo, —NO$_2$, —CO$_2$R$^9$, —N(R$^9$R$^{10}$) and a fused benzo group;

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or pamoate, salicylate and stearate. Similarly pharmaceutically acceptable cations include, but are not limited to sodium, potassium, calcium, aluminum, lithium and ammonium.

In the compounds of the present invention it is preferred that:
R$^1$ is selected from the group consisting of:
(1) phenyl, unsubstituted or substituted with one or more of R$^6$, R$^7$ and R$^8$, wherein R$^6$, R$^7$ and R$^8$ are as defined below;
R$^2$ is selected from the group consisting of:
(1) C$_{1-6}$ alkyl, unsubstituted or substituted with one or more of the substituents selected from:
(a) —NR$^9$R$^{10}$, wherein R$^9$ and R$^{10}$ are independently selected from:
(i) hydrogen,
(ii) phenyl, (iii) $C_{1-6}$ alkyl, unsubstituted or substituted with one or more of the substituents selected from:
(A) hydroxy,
(B) oxo,
(C) $C_{1-6}$ alkoxy,
(D) phenyl-$C_{1-3}$ alkoxy,
(E) phenyl,
(F) —CN,
(G) halo,
(H) —NR$^{14}$R$^{15}$, wherein R$^{14}$ and R$^{15}$ are independently selected from hydrogen, $C_{1-6}$ alkyl, and phenyl,
(I) -heteroaryl, wherein heteroaryl is selected from the group consisting of:
(a) furanyl,
(b) pyrrolyl,
(c) pyridyl,
(d) imidazolyl,
(e) oxadiazolyl,
(f) pyrazolyl,
(g) triazolo,
(h) tetrazolo,
(i) pyrimidyl,
(j) oxazolo,
(k) isooxazolo,
(l) thiazolo, and
(m) thiadiazolo, and wherein the heteroaryl is unsubstituted or substituted with one or more substituent(s) selected from:
(I) $C_{1-6}$ alkyl,
(II) $C_{1-6}$ alkoxy,
(III) —NR$^{14}$R$^{15}$, wherein R$^{14}$ and R$^{15}$ are as defined above,
(IV) halo, and
(V) trifluoromethyl;
(b) —NR$^9$COR$^{10}$ wherein R$^9$ and R$^{10}$ are as defined above,
(c) —NR$^9$CO$_2$R$^{10}$, wherein R$^9$ and R$^{10}$ are as defined above,
(d) —NR$^{14}$CONR$^9$R$^{10}$, wherein R$^9$, R$^{10}$ and R$^{14}$ are as defined above,
(e) —CONR$^9$R$^{10}$, wherein R$^9$ and R$^{10}$ are as defined above,
(f) —COR$^9$, wherein R$^9$ is as defined above,
(g) —CO$_2$R$^9$, wherein R$^9$ is as defined above; and
(2) —R$^9$, wherein R$^9$ is as defined above, with the proviso that R$^9$ is other than hydrogen or phenyl;
R$^3$ and R$^4$ are hydrogen;
R$^6$, R$^7$ and R$^8$ are independently selected from the group consisting of:
(1) hydrogen,
(2) $C_{1-6}$ alkyl, unsubstituted or-substituted with one or more of the substituents selected from:
(a) hydroxy,
(b) $C_{1-6}$ alkoxy,
(3) $C_{2-6}$ alkenyl,
(4) $C_{2-6}$ alkynyl,
(5) phenyl,
(6) halo,
(7) —CN,
(8) —CF$_3$,
(9) —OCF$_3$,
(10) hydroxy, and
(11) $C_{1-6}$alkoxy,
R$^{11}$, R$^{12}$ and R$^{13}$ are independently selected from the group consisting of:
(1) hydrogen,
(2) $C_{1-6}$ alkyl,
(3) $C_{2-6}$ alkenyl,
(4) $C_{2-6}$ alkynyl,
(5) halo,
(6) —CF$_3$, and
(7) $C_{1-6}$alkoxy;
X is —CH(R$^5$)—, wherein R$^5$ is hydrogen;
Y is selected from the group consisting of:
(1) —O—, and
(2) —N(R$^9$)—, wherein R$^9$ is as defined above.

An embodiment of the novel compounds of this invention is that wherein R$^1$ is phenyl of structural formula:

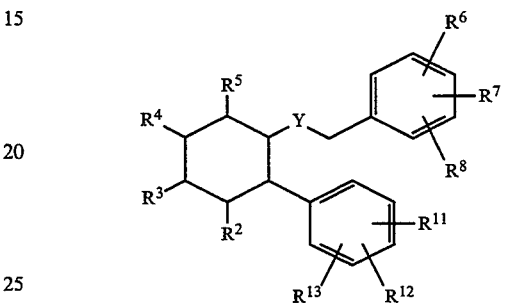

or a pharmaceutically acceptable salt thereof, wherein R$^2$, R$^3$, R$^4$, R$^5$, R$^6$, R$^7$, R$^8$, R$^{11}$, R$^{12}$, R$^{13}$ and Y are as defined above.

Another specific embodiment of the novel compounds of the present invention is that wherein Y is —O—.

Another embodiment of the novel compounds of the present invention is that wherein Y is selected from the group consisting of:
(1) —N(R$^9$)—, wherein R$^9$ is as defined above,
(2) —N(COR$^9$)—, wherein R$^9$ is as defined above,
(3) —N(CO$_2$R$^9$)—, wherein R$^9$ is as defined above, and
(4) —N(CONR$^9$R$^{10}$)—, wherein R$^9$ and R$^{10}$ are as defined above.

Specific compounds within the scope of the present invention include:
1) 3-(SR)-(3,5-bis(trifluoromethyl)benzyloxy)-2-(SR)-phenyl-1-( SR )-cyclohexylacetamide;
2) 3-(SR)-(3,5-bis(trifluoromethyl)benzyloxy)-2-(SR)-phenyl-1-(SR)-cyclohexylacetic acid, 3-(aminomethyl)-pyridine carboxamide;
3) 3-(SR)-(3,5-bis(trifluoromethyl)benzyloxy)-2-(SR)-phenyl-1-(SR)-cyclohexylacetic acid, 4-(aminomethyl)pyridine carboxamide;
4) α-aminocarbonylamino-3-(SR)-(3,5-bis(trifluoromethyl)benzyloxy)-2-(SR)-phenyl-1-(SR)-methylcyclohexane; and
5) α-3-(pyridylmethyl)aminocarbonylamino-3-(SR)-(3,5-bis(trifluoromethyl)benzyloxy)-2-(SR)-phenyl-1-(SR)-methylcyclohexane;
or a pharmaceutically acceptable salt thereof.

TACHYKININ ANTAGONISM ASSAY

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assay.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electropotation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electropotation in 800 ul of transfection buffer suplemented with 0.625 mg/ml Herring sperm DNA at 300 V and 950 uF using the IBI GENEZAPPER (IBI). The transfected cells were incubated in CHO media [10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)]in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific 125I-SP binding (approximately 50,000 to 200,000 cells). In the binding assay, 200 ul of cells were added to a tube containing 20 ul of 1.5 to 2.5 nM of $^{125}$I-SP and 20 µl of unlabeled substance p or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM$MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

The compounds of the present invention are useful in the prevention and treatment of a wide variety of clinical conditions which are characterized by the presence of an excess of tachykinin, in particular substance P, activity.

These conditions may include disorders of the central nervous system such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis and amyotrophic lateral sclerosis and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions especially the transmission of pain in migraine. Hence, these compounds are readily adapted to therapeutic use for the treatment of physiological disorders associated with an excess of tachykinins, especially substance P, and as substance P antagonists the control and/or treatment of any of the aforesaid clinical conditions in mammals, including humans.

The compounds of the present invention are particularly useful in the treatment of pain or nociception and/or inflammation and disorders associated therewith such as, for example: neuropathy, such as diabetic or peripheral neuropathy and chemotherapy-induced neruopathy; asthma; osteoarthritis; rheumatoid arthritis; and especially migraine.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. The dose will vary from patient to patient depending upon the nature and severity of disease, the patient's weight, special diets then being followed by a patient, concurrent medication, and other factors which those skilled in the art will recognize.

In the treatment of a condition associated with an excess of tachykinins, an appropriate dosage level will generally be about 0.001 to 50 mg per kg patient body weight per day which can be administered in single or multiple doses. Preferably, the dosage level will be about 0.01 to about 25 mg/kg per day; more preferably about 0.05 to about 10 mg/kg per day. For example, in the treatment of conditions involving the neruotransmission of pain sensations, a suitable dosage level is about 0.001 to 25 mg/kg per day, preferably about 0.0.05 to 10 mg/kg per day, and especially about 0.005 to 5 mg/kg per day. The compounds may be administered on a regimen of 1 to 4 times per day, preferably once or twice per day.

Several methods for preparing the compounds of this invention are illustrated in the following Schemes and Examples wherein $R^1$, $R^2$, $R^3$, $R^4$, $R^5$, $R^6$, $R^7$, $R^8$, $R^9$ and $R^{10}$ are as defined above, and n is 0, 1 or 2.

TABLE 1

ABBREVIATIONS USED IN SCHEMES AND EXAMPLES

| Reagents: | |
|---|---|
| Et₃N | triethylamine |
| Ph₃P | triphenylphosphine |
| TFA | trifluoroacetic acid |
| NaOEt | sodium ethoxide |
| DCC | N,N'-dicyclohexylcarbodiimide |
| DCU | N,N'-dicyclohexylurea |
| CDI | 1,1'-carbonyldiimidazole |
| MCPBA | m-chloroperbenzoic acid |
| DBU | 1,8-diazabicyclo[5.4.0]undec-7-ene |
| Cbz-Cl | benzyl chloroformate |
| iPr₂NEt or DIEA | N,N-diisopropylethylamine |
| NHS | N-hydroxysuccinimide |
| DIBAL | diisobutylaluminum hydride |
| Me₂SO₄ | dimethyl sulfate |
| HOBt | 1-hydroxybenzotriazole hydrate |
| EDAC | 1-ethyl-3-(3-dimethylaminopropyl)carbodiimide hydrochloride |
| Solvents: | |
| DMF | dimethylformamide |
| THF | tetrahydrofuran |
| MeOH | methanol |
| EtOH | ethanol |
| AmOH | n-amyl alcohol |
| AcOH | acetic acid |
| MeCN | acetonitrile |
| DMSO | dimethyl sulfoxide |
| Others: | |
| Ph | phenyl |
| Ar | aryl |
| Me | methyl |
| Et | ethyl |
| iPr | isopropyl |
| Am | n-amyl |
| Cbz | carbobenzyloxy (benzyloxycarbonyl) |
| Boc | tert-butoxycarbonyl |
| PTC | phase transfer catalyst |
| cat. | catalytic |
| FAB-MS | fast atom bombardment mass spectrometry |
| rt | room temperature |

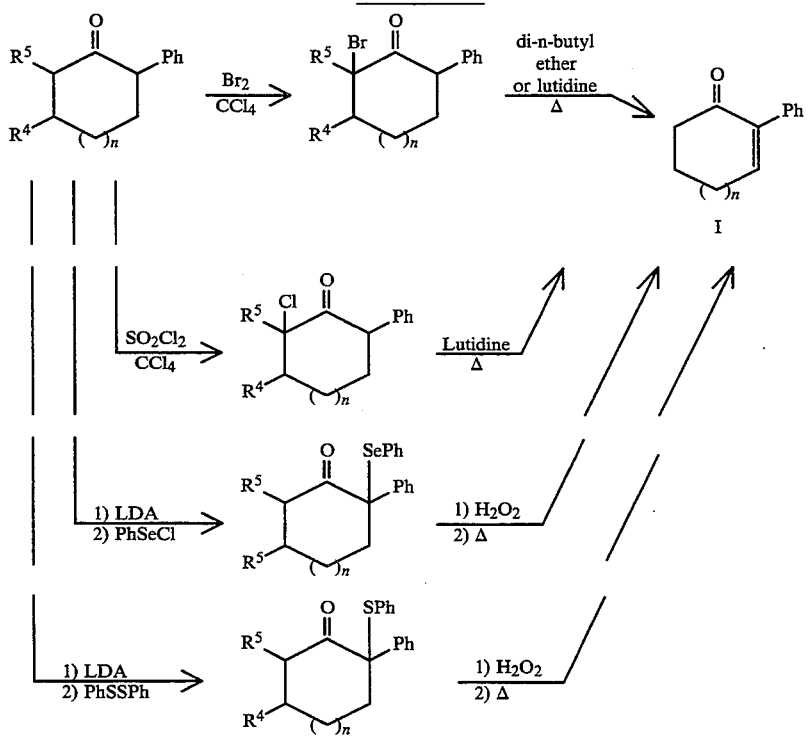

SCHEME I

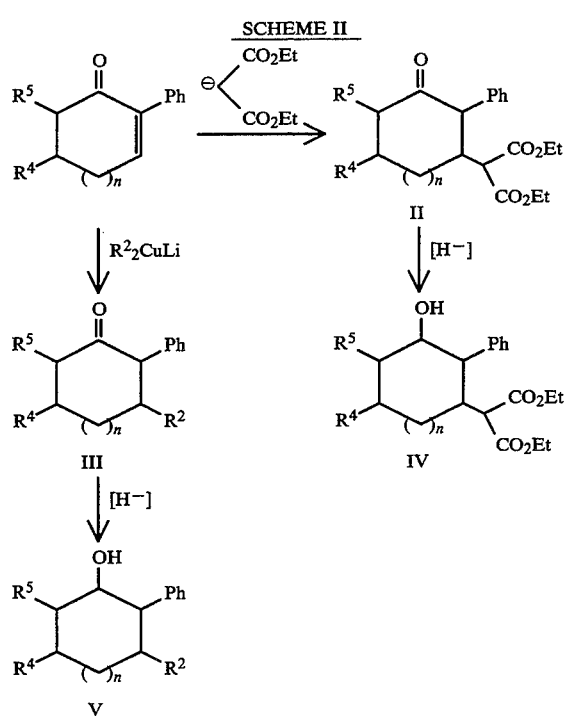
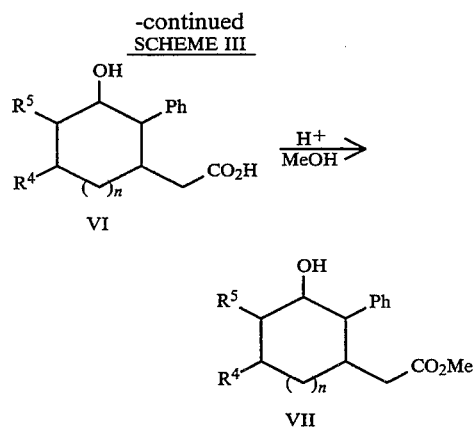
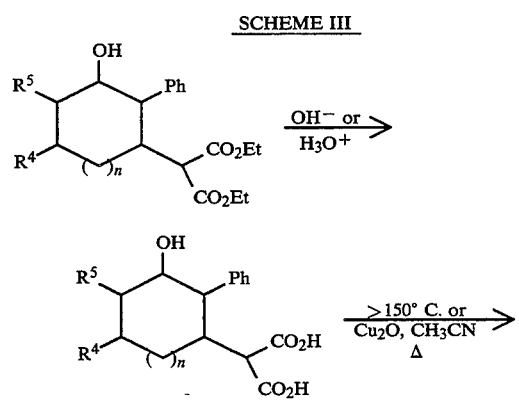
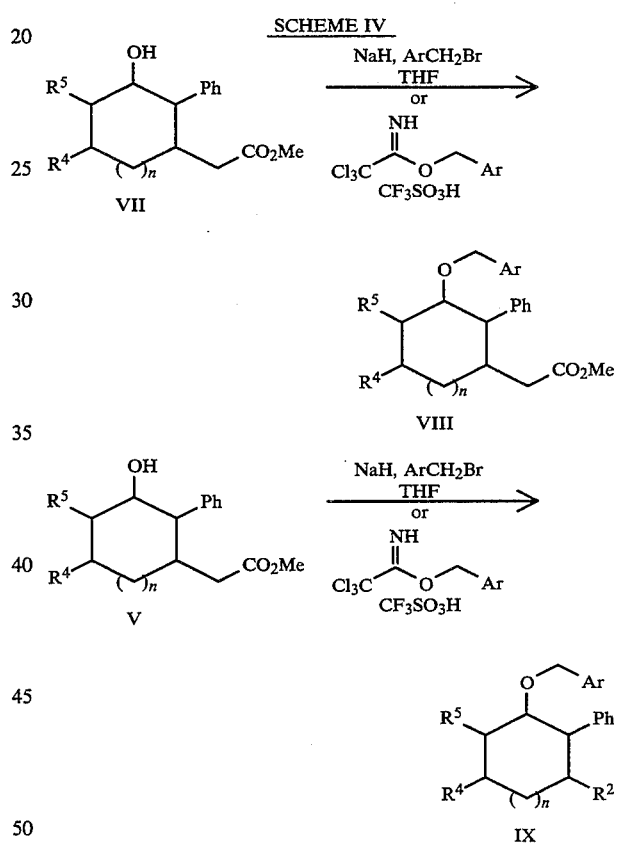
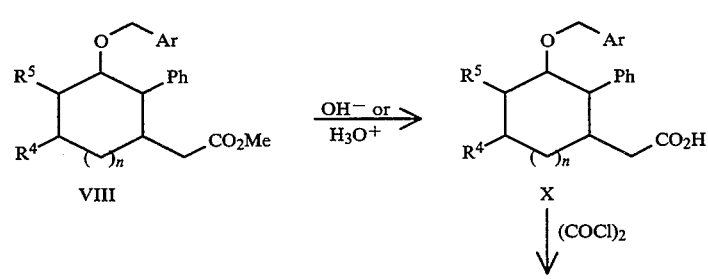

SCHEME V

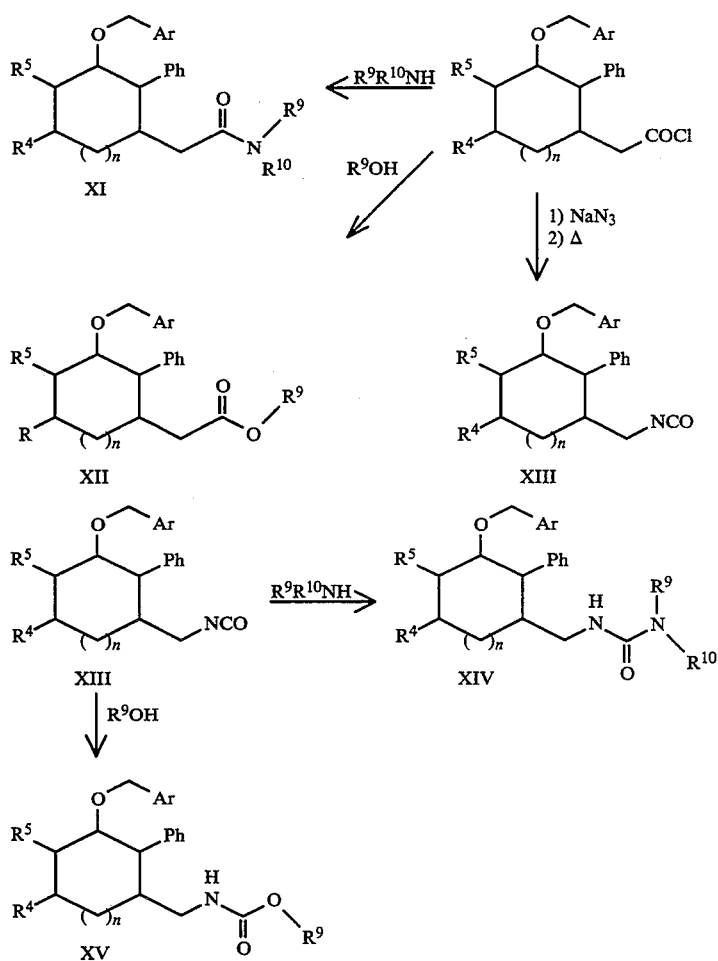

Preparation of carbocycle containing substance P antagonists may be accomplished according to the general route shown in Schemes I–V. As shown in Scheme I, treatment of commercially available 2-phenylcyclohexanone (or with a 2-arylcyclohexanone, wherein aryl is phenyl substituted with $R^{11}$, $R^{12}$ and $R^{13}$) with bromine results in predominant formation of a mixture of the 6-phenyl 2-bromocyclohexanones (as reported by Miller and Wong in *Tetrahedron*, 1972, 28, 2369). Thermolysis of this species in 2,6-lutidine or di-n-butyl ether results in dehydrohalogenation to cyclohexenone I. Chlorination with sulfuryl chloride followed by elimination in refluxing 2,6-lutidine to provide I has also been reported (Woods and Scotti in *J. Org. Chem.* 1961, 21, 312). Unsaturated ketone I may also be prepared by introduction of an α-selenophenyl group by reacting the enolate of the saturated ketone with phenylselenenyl chloride followed by low temperature oxidation with hydrogen peroxide and elimination at room temperature (see "Selenium Reagents and Intermediates in Organic Synthesis", C. Paulmier, Pergamon Press:1986, pages 84–101 and 125–143). Compound I may also be prepared by α-sulfenylation of the enolate of the saturated ketone with diphenyl disulfide folowed by oxidation with hydrogen peroxide and thermolysis above 100° C. (see Trost in *Chem. Reviews*, 1978 78,363). Many oxidants in addition to hydrogen peroxide are known that will transform the selenides and sulfides to their respective oxides (see for example the above cited references).

Michael reaction of the anion of diethyl malonate to enone I provides the adduct II (see Ginsburg and Pappo *Journal of the Chemical Society*, 1951, 938), as shown in Scheme II. Many types of alkyl and aryl groups at $R^2$ may be introduced to give III by exposing the enone to the requisite lithium dialkyl or diaryl cuprate (see G. Posner in Organic Reactions, Volume 19, W. G. Dauben Editor-in-Chief, Wiley:1972, pages 1–114) or to other copper-based anionic reagents. The products would be a mixture of cis- and trans- isomers at the 2- and 3- positions, and these may be separated by conventional methods, i.e. chromatography, fractional distillation or fractional crystallization.

Reduction to the alcohols IV and V may be accomplished with many active hydride reagents, for example lithium aluminum hydride, sodium borohydride, diisobutylaluminum hydride, diborane, and lithium tri-sec-butylborohydride (available commercially as L-Selectride ®). While the first 4 reagents listed would be expected to give mixtures of stereoisomers at the alcohol center, it is known that L-Selectride reduction of cyclohexanones gives predominantly product with the cis stereochemistry relative to a bulky alpha-substituent (see Brown and Krishnamurthy, *Journal of the American Chemical Society*, 1972, 94, 7159). Separation of the product isomers may be carried out by conventional means, for example by chromatography or fractional crystallization.

As shown in Scheme III, conversion of the malonate side chain of IV to an acetic acid subunit may be carried out by hydrolysis of the diester with acid or base (followed by neutralization) to the corresponding diacid. Thermal decarboxylation generally occurs above 150° C. to provide the acetic acid side chain. An alternative method, which is especially useful for compounds which are unstable at high temperatures, is exposure of the diacid to a catalytic amount of copper(I) oxide in refluxing acetonitrile under an inert atmosphere, which provides the monoacid VI in good yield (see Toussaint et al, *Synthesis*, 1986, 1029). Reesterification under standard conditions, for example refluxing methanol with a catalytic amount of a mineral acid or a sulfonic acid, or exposure to etherial dizaomethane, provides the methyl ester VII.

As shown in Scheme IV, alkylation of the alcohol of V or VII through formation of the lithium, sodium or potassium salt, for example by exposure to lithium diisopropylamide, sodium hydride or potassium hydride, respectively, followed by treatment with the requisite benzyl halide (wherein Ar is phenyl, unsubstituted or substituted with $R^6$, $R^7$ and $R^8$) provides the benzyl ethers VIII and IX. The reaction may also be carried out under mildly acidic conditions through the use of the appropriately substituted benzyl trichloroacetimidate (wherein Ar is as defined above) in the presence of a catalytic amount of trifluoromethanesulfonic acid (see Widmer *Synthesis* 1987, 568).

As shown in Scheme V, hydrolysis of the ester of VIII can be carried out under basic or acidic conditions to provide the free acid X. Formation of the acid chloride with oxalyl chloride, thionyl chloride or related reagents followed by exposure to a substituted amine $R^9R^{10}NH$ or with alcohol $R^9OH$ provides the amide XI or the ester XII. Alternatively, exposure of the acid chloride to sodium azide followed by brief heating above 70° C. provides the isocyanate XIII. Treatment of XIII with amine $R^9R^{10}NH$ or with alcohol $R^9OH$ gives urea XIV or carbamate XV.

It is to be understood that many other derivatives of VIII, IX, X and XIII can be prepared, including alicyclics, aromatics, and heterocycles, and these may be mono or multiply substituted with usual groups.

The object compounds of Formula I obtained according to the reactions as explained above may be isolated and purified in a conventional manner, for example, extraction, precipitation, fractional crystallization, recrystallization, chromatography, and the like.

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, pictate, pivalate, propionate, succinate, tartrate, tosylate, and undecanoate. Base salts include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vaCuO or by freeze drying or by exchanging the anions of an existing salt for another anion on a suitable ion exchange resin.

Although the reaction schemes described herein are reasonably general, it will be understood by those skilled in the art of organic synthesis that one or more functional groups present in a given compound of formula I may render the molecule incompatible with a particular synthetic sequence. In such a case an alternative route, an altered order of steps, or a strategy of protection and deprotection may be employed. In all cases the particular reaction conditions, including reagents, solvent, temperature, and time, should be chosen so that they are consistent with the nature of the functionality present in the molecule.

The following examples are given for the purpose of illustrating the present invention and shall not be construed as being limitations on the scope or spirit of the instant invention.

EXAMPLE 1

3-(SR)-(3,5-Bis(trifluoromethyl)benzyloxy)-2-(SR)-phenyl-1-(SR)-cyclohexylacetamide

Step A) 2-Bromo-6-phenylcyclohexanone

A solution of 15 g (86 mmole) of 2-phenylcyclohexanone in 60 mL of carbon tetrachloride at −5° C. was treated via rapid dropwise addition with a solution of 14.4 g (90 mmole) of bromine in 70 mL of carbon tetrachloride so as to maintain the reaction temperature below 5° C. The color disappeared rapidly. The mixture was concentrated in vacuo to a brown solid and the solid triturated with methanol. The resulting white solid was collected by filtration to provide 9.55 g of product. After cooling the mother liquor at −25° C., an additional 5.2 g of solid was obtained, for a total yield of 68%, a portion of which was carried on directly in Step B below.

Step B) 2-Phenyl-2-cyclohexenone

A suspension of 4.97 g (19.6 mmole) of 2-bromo-6-phenylcyclohexanone in 120 mL of di-n-butyl ether was heated at 175° C. for 7 hours, at which point evolution of gaseous HBr had essentially ceased. The mixture was concentrated in vacuo and the residue purified by flash chromatography with 75:25 methylene chloride: hexanes to provide 2.69 g (80%) of a white solid.

$^1$H NMR (CDCl$_3$, 400 MHz, ppm): δ2.15–2.25 (pentet, 2H), 2.50–2.60 (m, 4H), 7.03 (t, 1H), 7.25–7.35 (m, 5H).

Step C) Trans diethyl 2-phenyl-3-oxo-cyclohexyl-malonate

To 1 mL of ethanolic sodium ethoxide under nitrogen (prepared from 34 mg (1.45 mmole) of sodium metal in 1 mL of dry ethanol) was added 1.75 mL (11.6 mmole) of diethyl malonate and then 1.00 g (5.8 mmole) of 2-phenyl-2-cyclohexenone and the mixture was stirred under nitrogen in an oil bath at 60° C. for 3 hr. After stirring at room temperature for an additional 16 hr, the mixture was treated with 0.084 mL (1.45 mmole) of acetic acid and partly concentrated in vacuo. The residue was purified by flash chromatography on 220 g of silica gel eluting with 7 L of 8:1 hexanes: ethyl acetate to provide 1.50 g (78%) of pure product and 0.16 g (8%) of product containing minor polar byproducts.

Mass Spectrum (FAB): m/Z 333 (M+H, 4%), 331 (6%), 173 (100%), 161 (50%).

$^1$H NMR (CDCl$_3$, 400 MHz, ppm): δ1.19 (t, 3H), 1.24 (t, 3H), 1.70–1.85 (m, 1H), 2.02 (qd, 1H), 2.10–2.20 (m, 2H), 2.44 (td, 1H), 2.55 (din, 1H), 2.68 (tt, 1H), 3.09 (d, 1H), 3.74 (d, 1H), 4.00–4.23 (m, 4H), 7.07 (appd, 2H), 7.25–7.35 (m, 3H).

Step D) Diethyl 2-(SR)-phenyl-3-(SR)-hydroxy-(SR)-cyclohexlmalonate

A solution of 1.50 g (4.51 mmole) of transdiethyl 2-phenyl-3-oxo-cyclohexylmalonate in 20 mL of dry THF under nitrogen was cooled to −75° C. and was treated with 4.65 mL (4.65 mmole) of a 1M solution of L-Selectride® in THF. After 1 hr, the mixture was warmed to −40° C. and was treated with 10 mL of ethyl acetate and 8 mL of 10% aqueous sodium carbonate. After 5 min more, the reaction was placed in an ice bath and 4 mL of water was added followed by cautious addition of 2 mL of 30% hydrogen peroxide. After stirring for 30 min, the mixture was transferred to a separatory funnel and 15 mL of water and 20 mL of ethyl acetate plus 20 mL of hexanes was added, the phases were separated and the aqueous layer extracted with 80 mL of 1:1 hexanes: ethyl acetate. Each extract was washed with 15 mL of water and 15 mL of brine and the pooled organic phase was dried over sodium sulfate and concentrated in vacuo. The residue was purified by flash chromatography on 130 g of silica eluting with 3.5 L of 100:0.35 methylene chloride: methanol to give 1.02 g (67%) of pure product and 0.34 g of product containing less polar material.

Mass Spectrum (FAB): m/Z 335 (M+H, 100%), 317 (45%), 289 (30%), 243 (70%), 225 (50%), 197 (90%), 173 (35%), 157 (55%).

$^1$H NMR (CDCl$_3$, 400 MHz, ppm): δ1.15–1.25 (overlapping t, 6H), 1.45 (br s, 1H), 1.50–1.65 (m, 3H), 1.75–1.90 (m, 1H), 1.90–2.00 (m, 2H), 2.82–2.93 (m, 2H), 3.25 (d, 1H), 3.88 (br s, 1H), 4.00–4.15 (m, 4H), 7.20–7.28 (m, 3H), 7.30–7.35 (m, 2H).

Step E) 2-(SR)-Phenyl-3-(SR)-hydroxy-(SR)-cyclohexylmalonic acid

A solution of 0.87 g (2.6 mmole) of diethyl-2-(SR)-phenyl-3-(SR)-hydroxy-(SR)-cyclohexylmalonate in 12 mL of THF and 7 mL of water was treated with 3.1 mL (7.8 mmole) of 10% aqueous sodium hydroxide and the mixture was heated in an oil bath at 70° C. under nitrogen for 24 hr. The mixture was cooled, 10 mL of water was added and the pH was adjusted to 2 with 2N aqueous HCl. The mixture was extracted with 3×35 mL of ethyl acetate, and the organic layer was dried with magnesium sulfate, filtered and concentrated in vacuo to give 700 mg of a light yellow foam. This material was carried on in Step F below.

Step F) 2-(SR)-Phenyl-3-(SR)-hydroxy-(SR)-cyclohexylacetic acid

A suspension of ca. 700 mg (2.52 mmole) of 2-(SR)-phenyl-3-(SR)-hydroxy-(SR)-cyclohexylmalonic acid in 55 mL of acetonitrile was degassed with nitrogen for 10 min and then 18 mg (0.13 mmole) of copper (I) oxide was added under nitrogen and the mixture was heated at reflux for 40 hr under nitrogen. The solution was cooled and concentrated in vacuo, and the residue was taken up in 50 mL of water containing 0.4 mL of 2N HCl and 45 mL of ether. The layers were separated and the aqueous layer was extracted with 2×50 mL of ether. The pooled organic extracts were dried over magnesium sulfate, filtered and concentrated in vacuo. The residue was purified by flash chromatography on 67 g of silica eluting with 1 L of 100:3:0.1 methylene chloride:methanol: acetic acid to provide 530 mg (90%) of a light yellow oil that crystallized on standing.

Mass Spectrum (FAB): m/Z 289 (10%), 245 (40%), 217 (M-OH, 35%), 199 (45%), 171 (35%), 157 (100%), 129 (40%).

$^1$H NMR (CDCl$_3$, 400 MHz, ppm): δ1.16 (qd, 1H), 1.53–1.65 (m, 2H), 1.75–2.05 (m, 4H), 2.28 (dd, 1H), 2.49 (dd, 1H), 2.60–2.70 (m, 1H), 3.89 (d, 1H), 7.2–7.3 (3H), 7.30–7.38 (m, 2H).

Step G) Methyl 2-(SR)-phenyl-3-(SR)-hydroxy-(SR)-cyclohexylacetate

A solution of 0.53 g (2.26 mmole) of 2-(SR)-phenyl-3-(SR)-hydroxy-(SR)-cyclohexylacetic acid in 35 mL of methanol was treated with 22 mg (0.11 mmole) of p-toluenesulfonic acid monohydrate and the mixture was heated at reflux for 27 hr. The mixture was cooled, treated with 0.02 mL of triethylamine and concentrated in vacuo. The residue was purified by flash chromatography on 67 g of silica eluting with 1.6 L of 8:1 hexanes:ethyl acetate to give 0.506 g (90%) of an oil.

$^1$H NMR (CDCl$_3$, 400 MHz, ppm): δ1.11 (qd, J=11.5, 3.3, 1H), 1.45–1.65 (m, 3H), 1.75–2.00 (m, 4H), 2.02 (dd, J=15.1, 3.3, 1H), 2.47 (dd, J=12.1, 2.3, 1H), 2.58–2.68 (m, 1H), 3.56 (s, 3H), 3.85 (narrow m, 1H), 7.17–7.27 (m, 3H), 7.28–7.35 (m, 2H).

Step H) Methyl 3-(SR)-(3,5-bis(trifluoromethyl)-benzyloxy)-2-(SR)-phenyl-1-(SR)-cyclohexylacetate A solution of 0.56 g (2.26 mmole) of methyl 2-(SR)-phenyl-B-(SR)-hydroxy-(SR)-cyclohexylacetate in 16 mL of dry THF under nitrogen was treated with 0.166 g (0.45 mmole) of tetrabutylammonium iodide and 0.618 mL (3.38 mmole) of 3,5-bis(trifluoromethyl)benzyl bromide. The mixture was cooled to 0° C., 0.108 g (2.71 mmole) of 60% sodium hydride in mineral oil was added, and the cooling bath was removed. After 2 hr and after 6 hr, 0.005 mL aliquots of methanol were added, and stirring was continued at room temperature for a total of 24 hr. An additional 0.25 mL of 3,5-bis(trifluoromethyl)benzyl bromide was added and the reaction was stirred an additional 9 hr. The mixture was treated with 3 mL of water, several drops of aqueous HCl were added, and the pH was adjusted to ca. 7 with aqueous sodium bicarbonate. The solution was treated with 15 mL of water and the aqueous phase was extracted with 3×30 mL of ethyl acetate. The pooled organic extracts were dried over sodium sulfate, filtered and concentrated in vacuo. The residue was purified by flash chromatography on 67 g of silica with 1L of 20:1 hexanes:ethyl acetate to provide 0.54 g (50%) of product and ca. 0.28 g (ca. 50%) of recovered starting material.

Mass Spectrum (FAB): m/Z 383 (3%), 317 (8%), 231 (30%), 227 (100%), 199 (40%), 171 (25%), 157 (60%), 129 (40%).

$^1$H NMR (CDCl$_3$, 400 MHz, ppm): δ1.25 (qd, 1H), 1.48 (tm, 1H), 1.55–1.63 (m, 1H), 1.78 (tt, 1H), 1.84 (dd, 1H), 1.96 (br d, 1H), 2.13 (br d, 1H), 2.23 (dd, 1H), 2.48 (dd, 1H), 2.62–2.72 (m, 1H), 3.56 (s, 3H), 3.67 (br s, 1H), 4.08 (d, 1H), 4.53 (d, 1H), 7.20–7.30 (5H), 7.58 (s, 2H), 7.72 (s, 1H).

Step I)
3-(SR)-(3,5-Bis(trifluoromethyl)benzyloxy)-2-(SR)-phenyl-1-(SR)-cyclohexylacetic acid A mixture of 0.54 g (1.14 mmole) of methyl 3-(SR)-(3,5-bis(trifluoromethyl)benzyloxy)-2-(SR)-phenyl-1-(SR)-cyclohexylacetate in 6 mL of THF and 4 mL of water was treated with 1.37 mL of 10% aqueous sodium hydroxide, and the suspension was heated for 36 hr at 75° C. The solution was cooled and treated with 5 mL of water and the pH was adjusted to 1–2 with aqueous HCl. The mixture was extracted with 3×25 mL of ethyl acetate and the extracts were filtered and concentrated in vacuo to give 0.511 g (97%) of a clear oil.

Mass Spectrum (FAB): m/Z 921 (2M+1, 1%), 443 (M-OH, 8%), 317 (6%), 227 (ARCH$_2$, 60%), 217 (M-ArCH$_2$OH-OH+H, 100%), 199 (35%), 157 (40%).

$^1$H NMR (CDCl$_3$, 400 MHz, ppm): δ1.16 (qd, J=13.3, 3.8, 1H>, 1.40–1.52 (tm, 1H), 1.53–1.63 (m, 1H), 1.75 (tt, 1H), 1.84 (dd, 1H), 2.03 (br d, 1H), 2.13 (br d, 1H), 2.27 (dd, J=15.6, 3.2, 1H), 2.49 (dd, J=12.1, 2.5, 1H), 2.60–2.75 (m, 1H), 3.66 (d, J=2.1, 1H), 4.07 (d, J=12.2, 1H), 4.51 (d, J=12.2, 1H), 7.18–7.30 (m, 5H), 7.56 (s, 2H), 7.71 (s, 1H).

Step J)
3-(SR)-(3,5-Bis(trifluoromethyl)benzyloxy)-2-(SR)-phenyl-1-(SR)-Cyclohexylacetyl chloride A solution of 0.300 g (0.65 mmole) of 3-(SR)-(3,5-bis(trifluoromethyl)benzyloxy)-2-(SR)-phenyl-1-(SR)-cyclohexylacetic acid in 8 mL of dry methylene chloride was treated with 0.125 mL (1.43 mmole) of oxalyl chloride and then several drops of a dilute solution of DMF in methylene chloride, and the resulting mixture was stirred at room temperature for 30 min. The solution was concentrated by exposure to a stream of nitrogen and the residue was employed directly for Step K below.

Step K)
3-(SR)-(3,5-Bis(trifluoromethyl)benzyloxy)-2-(SR)-phenyl-1-(SR)-cyclohexylacetamide A solution of 0.156 g (0.33 mmole) of 3-(SR)-(3,5-bis(trifluoromethyl)benzyloxy)-2-(SR)-phenyl-1-(SR)-cyclohexylacetyl chloride in 1 mL of methylene chloride was treated with 4 mL of ammonia saturated methylene chloride. After one hr the solution was concentrated in vacuo and the residue purified by flash chromatography on 35 g of silica eluting with 1L of 100:1.6 methylene chloride:methanol to provide 0.150 g (100%) of a slowly crystallizing oil.

Mass Spectrum (FAB): m/Z 460 (M+H, 25%), 216 (M-ArCH$_2$OH-NH$_2$+H, 100%), 157 (30%).

$^1$H NMR (CDCl$_3$, 400 MHz, ppm): δ1.19 (qd, J=13.1, 3.8, 1H), 1.47 (tm, 1H), 1.59 (dm, 1H), 1.65–1.85 (m, 2H), 2.04–2.18 (m, 3H), 2.48 (dd, J=12.0, 2.4, 1H), 2.60–2.72 (m, 1H), 3.66 (d, J=2.2, 1H), 4.07 (d, J=12.4, 1H), 4.52 (d, J=12.4, 1H), 5.13 (br s, 1H), 5.41 (br s, 1H), 7.19–7.35 (m, 5H), 7.56 (s, 2H), 7.71 (s, 1H).

EXAMPLE 2

3-(SR)-(3,5-Bis(trifluoromethyl)benzyloxy)-2-(SR)-phenyl-1-(SR)-cyclohexylacetic acid, 3-(aminomethyl)pyridine carboxamide To a solution of 78 mg (0.16 mmole) of 3-(SR)-(3,5-bis(trifluoromethyl)benzyloxy)-2-(SR)-phenyl-1-(SR)-cyclohexylacetyl chloride (from Example 1, Step J above) in 2 mL of methylene chloride under nitrogen was added 0.066 mL (0.65 mmole) of 3-(aminomethyl)-pyridine, and the solution was stirred at room temperature. After 45 min, the mixture was purified by flash chromatography on 23 g of silica eluting with 500 mL of 100:1.8 methylene chloride: methanol to provide 79 mg (88%) of an oil that slowly crystallized.

Mass Spectrum (FAB): m/Z 551 (M+H, 100%), 306 (20%), 225 (18%).

$^1$H NMR (CDCl$_3$, 400 MHz, ppm): δ1.22 (qd, J=13.3, 3.7, 1H), 1.46 (tm, 1H), 1.55–1.65 (m, 1H), 1.80–1.95 (m, 3H), 1.97–2.05 (m, 1H), 2.10–2.20 (m, 2H), 2.48 (dd, J=12.1, 2.4, 1H), 2.65–2.75 (m, 1H), 4.07 (d, J=12.4, 1H), 4.27 (dd, J=15.0, 5.8, 1H), 4.38 (dd, J=15.0, 5.9, 1H), 4.51 (d, J=12.3, 1H), 5.43 (br t, 1H), 7.20–7.35 (m, 6H), 7.50–7.55 (m, 1H), 7.56 (s, 2H), 7.71 (s, 1H), 8.44 (d, J=1.8, 1H), 8.49 (dd, J=4.7, 1.6, 1H).

EXAMPLE 3

3-(SR)-(3,5-Bis(trifluoromethyl)benzyloxy)-2-(SR)-phenyl-1-(SR)-cyclohexylacetic acid, 4-(aminomethyl)pyridine carboxamide To a solution of 78 mg (0.16 mmole) of 3-(SR)-(3,5-bis(trifluoromethyl)benzyloxy)-2-(SR)-phenyl-1-(SR)-cyclohexylacetyl chloride (from Example 1, Step J above) in 2 mL of methylene chloride under nitrogen was added 0.066 mL (0.65 mmole) of 4-(aminomethyl)-pyridine, and the solution was stirred at room temperature. After 45 min, the mixture was purified by flash chromatography on 23 g of silica eluting with 500 mL of 100:2 methylene chloride: methanol to provide 88 mg (97%) of an oil that slowly crystallized.

Mass Spectrum (FAB): m/Z 551 (M+H, 100%), 306 (10%), 225 (15%).

$^1$H NMR (CDCl$_3$, 400 MHz, ppm): δ1.21 (qd, J=13.1, 3.8, 1H), 1.46 (tm, 1H), 1.55–1.65 (m, 1H), 1.70–1.85 (m, 2H), 1.97–2.05 (m, 2H), 2.14 (br d, 1H), 2.18 (dd, J=14.4, 3.5, 1H), 2.48 (dd, J=12.0, 2.5, 1H), 2.65–2.77 (m, 1H), 3.65 (d, J=2.2, 1H), 4.07 (d, J=12.4, 1H), 4.25 (dd J=15.8, 5.9, 1H), 4.34 (dd, J=15.8, 6.2, 1H), 4.51 (d, J=12.4, 1H), 5.84 (br t, 1H), 7.06 (d, J=5.9, 2H), 7.15–7.35 (m, 5H), 7.56 (s, 2H), 7.70 (s, 1H), 8.44 (m, 2H).

EXAMPLE 4

α-Aminocarbonylamino-3-(SR)-(3,5-bis(trifluoromethyl)benzyloxy)-2-(SR)-phenyl-1-(SR)-methylcyclohexane

Step A)

α-Isocyanato-3-(SR)-(3,5-bis(trifluoromethyl)benzyloxy)-2-(SR)-phenyl-1-(SR)-methylcyclohexane A solution of 123 mg (0.27 mmole) of 3-(SR)-(3,5-bis(-trifluoromethyl)benzyloxy)-2-(SR)-phenyl-1-(SR)-cyclohexylacetic acid (from Example 1, Step I above) in 1 mL of benzene was treated with 0.046 mL (0.53 mmole) of oxalyl chloride and one drop of a solution of one drop of DMF in 2 mL of benzene, and the solution was stirred under nitrogen for 40 min. The volatile components were removed in a stream of nitrogen and the residue was taken up in 1 mL of acetone. This solution was cooled to 0° C. and was treated with a solution of 35 mg (0.53 mmole) of sodium azide in 0.5 mL of water, and the resulting mixture was stirred at 0° C. for 45 min. The mixture was then poured into 5 mL of ice and water and 4 mL of benzene and the mixture was extracted with 2×5 mL of cold benzene. The combined organic layers were washed with 5 mL of ice cold brine and the organic layer was filtered through a pad of sodium sulfate. The resulting solution was partly concentrated in vacuo (bath temperature 26°–28° C.) to 1–2 mL volume and was flushed once with 8 mL of benzene. After careful concentration, the residue was taken up in 6 mL of benzene and was heated in an oil bath to 80° C. and held at that temperature for 30 min, during which time gas evolved. After cooling the solution was concentrated in vacuo to provide 115 mg of an oil, which was employed in Step B below.

Step B)

α-Aminocarbonylamino-3-(SR)-(3,5-bis(trifluoromethyl)benzyloxy)-2-(SR)-phenyl-1-(SR)-methylcyclohexane A solution of 56 mg (0.12 mmole) of α-isocyanato-3-(SR)-(3,5-Bis(trifluoromethyl)-benzyloxy)-2-(SR)-phenyl-1-(SR)-methylcyclohexane in 1 mL of methylene chloride was treated with 3 mL of ammonia-saturated methylene chloride at room temperature. After 1 hr, the solution was concentrated in vacuo and the residue purified by flash chromatography on 16 g of silica eluting with 400 mL of 100:2 methylene chloride: methanol to provide 54 mg (93%) of a white powder.

Mass Spectrum (FAB): m/Z $^1$H NMR (CDCl$_3$, 400 MHz, ppm): δ1.15 (qd, 1H), 1.43 (br t, 1H), 1.55–1.90 (m, 2H), 1.96 (br d, 1H), 2.11 (br d, 1H), 2.25–2.38 (m, 1H), 2.44 (dd, J=11.8, 2.2, 1H), 2.72–2.82 (m, 1H), 2.90–3.00 (m, 1H), 3.64 (s, 1H), 4.08 (d, J=12.2, 1H), 4.20–4.35 (br s, 2H), 4.45–4.55 (m, 2H), 7.18–7.35 (m, 5H), 7.57 (s, 2H), 7.71 (s, 1H).

EXAMPLE 5

α-3-(Pyridylmethyl)aminocarbonylamino-3-(SR)-(3,5-bis(trifluoromethyl)benzyloxy)-2-(SR)-phenyl-1-(SR)methylcyclohexane A solution of 56 mg (0.12 mmole) of α-isocyanato-3-(SR)-(3,5-bis(trifluotomethyl)benzyloxy)-2-( SR)-phenyl-1-( SR)-methylcyclohexane (from Example 4, Step A) in 1 mL of methylene chloride was treated with 0.037 mL (0.37 mmole) of 3-(aminomethyl)pyridine at room temperature. After 1 hr, the solution was concentrated in vacuo and the residue purified by flash chromatography on 16 g of silica eluting with 400 mL of 100:2.5 methylene chloride: methanol to provide 49mg (71%) of an oil.

Mass Spectrum (FAB): m/Z $^1$H NMR (CDCl$_3$, 400 MHz, ppm): δ1.14 (qd, 1H), 1.43 (tm, 1H), 1.55–1.80 (m, 3H), 1.94 (br dd, 1H), 2.11 (br d, 1H), 2.25–2.38 (m, 1H), 2.42 (dd, J=12.0, 2.4, 1H), 2.77–2.85 (m, 1H), 2.99 (m, 1H), 3.62 (d, J =2.2, 1H), 4.08 (d, J=12.4, 1H), 4.18–4.30 (m, 3H), 4.45–4.55 (m, 2H), 7.15–7.30 (m, 6H), 7.50–7.55 (m, 1H), 7.56 (s, 2H), 7.71 (s, 1H), 8.39–8.48 (m, 2H).

EXAMPLE 6

Typical Pharmaceutical Compositions Containing a Compound of the Invention

A: Dry Filled Capsules Containing 50 mg of Active Ingredient Per Capsule

| Ingredient | Amount per capsule (mg) |
| --- | --- |
| Active ingredient | 50 |
| Lactose | 149 |
| Magnesium stearate | 1 |
| Capsule (size No. 1) | 200 |

The active ingredient can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain the active ingredient (25 mg), pregelatinized starch USP (82 mg), microcrystalline cellulose (82 mg) and magnesium stearate (1 mg).

C: Suppository

Typical suppository formulations for rectal administration contain the active ingredient (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol.

D: Injection

A typical injectible formulation contains the acting ingredient sodium phosphate dibasic anhydrous (11.4 mg), benzyl alcohol (0.01 ml) and water for injection (1.0 ml).

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of structural formula:

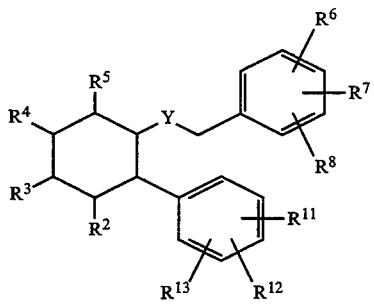

or a pharmaceutically acceptable salt thereof, wherein:
$R^2$ is selected from the group consisting of:
(1) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$, wherein $R^9$ and $R^{10}$ are independently selected from:
  (i) hydrogen,
  (ii) phenyl,
  (iii) C 1-6 alkyl, unsubstituted or substituted with one or more of the substituents selected from:
    (A) hydroxy,
    (B) oxo,
    (C) $C_{1-6}$ alkoxy,
    (D) phenyl-$C_{1-3}$ alkoxy,
    (E) phenyl,
    (F) —CN,
    (G) halo,
    (H) —$NR^{14}R^{15}$, wherein $R^{14}$ and $R^{15}$ are independently selected from hydrogen, $C_{1-6}$ alkyl, and phenyl,
  (I) -heteroaryl, wherein heteroaryl is selected from the group consisting of:
    (a) furanyl,
    (b) pyrrolyl,
    (c) pyridyl,
    (d) imidazolyl,
    (e) oxadiazolyl,
    (f) pyrazolyl,
    (g) triazolo,
    (h) tetrazolo,
    (i) pyrimidyl,
    (j) oxazolo,
    (k) isooxazolo,
    (l) thiazolo, and
    (m) thiadiazolo, and wherein the heteroaryl is unsubstituted or substituted with one or more substituent(s) selected from:
      (I) $C_{1-6}$ alkyl,
      (II) $C_{1-6}$ alkoxy,
      (III) —$NR^{14}R^{15}$, wherein $R^{14}$ and $R^{15}$ are as defined above,
      (IV) halo, and
      (V) trifluoromethyl;
(i) —$NR^9COR_{10}$, wherein $R^9$ and $R^{10}$ are as defined above,
(j) —$NR^9CO_2R^{10}$, wherein $R^9$ and $R^{10}$ are as defined above,
(k) —$NR^{14}CONR^9R^{10}$, wherein $R^9$, $R^{10}$ and $R^{14}$ are as defined above,
(l) —$CONR^9R^{10}$, wherein $R^9$ and $R^{10}$ are as defined above,
(m) —$COR^9$, wherein $R^9$ is as defined above,
(n) —$CO_2R^9$, wherein $R^9$ is as defined above,
(o) —$S(O)_n$-$R^9$, wherein n is 0, 1 or 2 and $R^9$ is as defined above; and
(2) —$R^9$, wherein $R^9$ is as defined above, with the proviso that $R^9$ is other than hydrogen or phenyl;
$R^3$ and $R^4$ are independently selected from the group consisting of:
(1) hydrogen;
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$NR^{14}CONR^9R^{10}$, wherein $R^9$, $R^{10}$ and $R^{14}$ are as defined above,
(l) —$CONR^9R^{10}$, wherein $R^9$ and $R^{10}$ are as defined above,
(m) —$COR^9$, wherein $R^9$ is as defined above,
(n) —$CO_2R^9$, wherein $R^9$ is as defined above;
(o) —$S(O)_n$-$R^9$, wherein n is 0, 1 or 2 and $R^9$ is as defined above,
(3) phenyl, unsubstituted or substituted with one or more of $R^6$, $R^7$ and $R^8$, wherein $R^6$, $R^7$ and $R^8$ are as defined below;
and the groups $R^3$ and $R^4$ may be joined together by a $C_{3-4}$alkyl or a $C_{3-4}$alkenyl to form a carbocyclic ring selected from the group consisting of:
(a) cyclopentyl,
(b) cyclohexyl,
(c) phenyl, and wherein the carbocyclic ring is unsubstituted or substituted with one or more substituents selected from:
  (i) $C_{1-6}$alkyl,
  (ii) $C_{1-6}$alkoxy,
  (iii) —$NR^9R^{10}$, wherein $R^9$ and $R^{10}$ are as defined above,
  (iv) halo, and
  (v) trifluoromethyl;
$R^5$ is independently selected from the definitions of $R^9$ and $R^{10}$, wherein $R^9$ and $R^{10}$ are as defined above,
$R^6$, $R^7$ and $R^8$ are independently selected from the group consisting of:
(1) hydrogen;
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo, (h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —NR$^{14}$CONR$^9$R$^{10}$, wherein R$^9$, R$^{10}$ and R$^{14}$ are as defined above,
(l) —CONR$^9$R$^{10}$, wherein R$^9$ and R$^{10}$ are as defined above,
(m) —COR$^9$, wherein R$^9$ is as defined above,
(n) —CO$^2$R$^9$, wherein R$^9$ is as defined above,
(o) —S(O)$_n$-R$^9$, wherein n is 0, 1 or 2 and R$^9$ is as defined above;
(3) C$_{2-6}$ alkenyl, unsubstituted or substituted with one or more of the substituent(s) selected from:
(a) hydroxy,
(b) oxo,
(c) C$_{1-6}$ alkoxy,
(d) phenyl-C$_{1-3}$ alkoxy,
(e) phenyl,
(f) —CN,
(g) halo,
(h) —CONR$^9$R$^{10}$ wherein R$^9$ and R$^{10}$ are as defined above,
(i) —COR$^9$ wherein R$^9$ is as defined above,
(j) —CO$_2$R$^9$, wherein R$^9$ is as defined above;
(4) C$_{2-6}$ alkynyl;
(5) phenyl, unsubstituted or substituted with one or more of the substituent(s) selected from:
(a) hydroxy,
(b) C$_{1-6}$ alkoxy,
(c) C$_{1-6}$ alkyl,
(d) C$_{2-5}$ alkenyl,
(e) halo,
(f) —CN,
(g) —NO$_2$,
(h) —CF$_3$,
(i) —(CH$_2$)$_n$-NR$^9$R$^{10}$, wherein n, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —NR$^{14}$CONR$^9$R$^{10}$, wherein R$^9$, R$^{10}$ and R$^{14}$ are as defined above,
(m) —CONR$^9$R$^{10}$, wherein R$^9$ and R$^{10}$ are as defined above,
(n) —COR$^9$, wherein R$^9$ is as defined above,
(o) —CO$_2$R$^9$, wherein R$^9$ is as defined above,
(p) —S(O)$_n$-R$^9$, wherein n is 0, 1 or 2 and R$^9$ is as defined above;
(6) halo,
(7) —CN,
(8) —CF$_3$,
(9) —OCF$_3$,
(10) —NO2,
(11) hydroxy,
(12) C$_{1-6}$ alkoxy,
(13) —COR$^9$, wherein R$^9$ is as defined above,
(14) —CO$_2$R$^9$, wherein R$^9$ is as defined above;
(15) —CONR$^9$COR$^{10}$, wherein R$^9$ and R$^{10}$ are as defined above,
(16) —SR$^{14}$, wherein R$^{14}$ is as defined above,
(17) —SOR$^{14}$, wherein R$^{14}$ is as defined above,
(18) —SO$_2$R$^{14}$, wherein R$^{14}$ is as defined above,
(19) —NR$^9$R$^{10}$, wherein R$^9$ and R$^{10}$ are as defined above,
(20) —NR$^9$COR$^{10}$, wherein R$^9$ and R$^{10}$ are as defined above,
(21) —NR$^9$CO$_2$R 10, wherein R$^9$ and R$^{10}$ are as defined above, and
(22) —NR$^{14}$CONR$^9$, R$^{10}$, wherein R$^9$, R$^{10}$ and R$^{14}$ are as defined above;
R$^{11}$, R$^{12}$ and R$^{13}$ are independently selected from the definitions of R$^6$, R$^7$ and R$^8$;
Y is selected from the group consisting of:
(1) —O—,
(2) —S—,
(3) —N(R$^9$)—, wherein R$^9$ is as defined above,
(4) —N(COR$^9$)—, wherein R$^9$ is as defined above,
(5) —N(CO$_2$R$^9$)—, wherein R$^9$ is as defined above, and
(6) —N(CONR$^9$R$^{10}$)—, wherein R$^9$ and R$^{10}$ are as defined above.

2. The compound of claim 1 wherein:
R$^2$ is selected from the group consisting of:
(1) C$_{1-6}$ alkyl, unsubstituted or substituted with one or more of the substituents selected from:
(a) —NR$^9$R$^{10}$, wherein R$^9$ and R$^{10}$ are independently selected from:
(i) hydrogen,
(ii) phenyl,
(iii) C$_{1-6}$ alkyl, unsubstituted or substituted with one or more of the substituents selected from:
(A) hydroxy,
(B) oxo,
(C) C$_{1-6}$ alkoxy,
(D) phenyl-C$_{1-3}$ alkoxy,
(E) phenyl,
(F) —CN,
(G) halo,
(H) —NR$^{14}$R$^{15}$, wherein R$^{14}$ and R$^{15}$ are independently selected from hydrogen, C$_{1-6}$ alkyl, and phenyl,
(I) heteroaryl, wherein heteroaryl is selected from the group consisting of:
(a) furanyl,
(b) pyrrolyl,
(c) pyridyl,
(d) imidazolyl,
(e) oxadiazolyl,
(f) pyrazolyl,
(g) triazolo,
(h) tetrazolo,
(i) pyrimidyl,
(j) oxazolo,
(k) isooxazolo,
(l) thiazolo, and
(m) thiadiazolo, and wherein the heteroaryl is unsubstituted or substituted with one or more substituent(s) selected from:
(I) C$_{1-6}$ alkyl,
(II) C$_{1-6}$ alkoxy,
(III) —NR$^{14}$R$^{15}$, wherein R$^{14}$ and R$^{15}$ are as defined above,
(IV) halo, and
(V) trifluoromethyl;
(b) —NR$^9$COR$_{10}$, wherein R$^9$ and R$^{10}$ are as defined above,
(c) —NR$^9$CO$_2$R$^{10}$, wherein R$^9$ and R$^{10}$ are as defined above,
(d) —NR$^{14}$CONR$^9$R$^{10}$, wherein R$^9$, R$^{10}$ and R$^{14}$ are as defined above,
(e) —CONR$^9$R$^{10}$, wherein R$^9$ and R$^{10}$ are as defined above,
(f) —COR$^9$, wherein R$^9$ is as defined above, (g) —$CO_2R^9$, wherein $R^9$ is as defined above; and
(2) —$R^9$, wherein $R^9$ is as defined above, with the proviso that $R^9$ is other than hydrogen or phenyl;
$R^3$ and $R^4$ are hydrogen;
$R^6$, $R^7$ and $R^8$ are independently selected from the group consisting of:
(1) hydrogen,
(2) $C_{1-6}$ alkyl, unsubstituted or substituted with one or more of the substituents selected from:
  (a) hydroxy,
  (b) $C_{1-6}$ alkoxy,
(3) $C_{2-6}$ alkenyl,
(4) $C_{2-6}$ alkynyl,
(5) phenyl,
(6) halo,
(7) —CN,
(8) —$CF_3$,
(9) —$OCF_3$,
(10) hydroxy, and
(11) $C_{1-6}$ alkoxy,
$R^{11}$, $R^{12}$ and $R^{13}$ are independently selected from the group consisting of:
(1) hydrogen,
(2) $C_{1-6}$ alkyl,
(3) $C_{2-6}$ alkenyl,
(4) $C_{2-6}$ alkynyl,
(5) halo,
(6) —$CF_3$, and
(7) $C_{1-6}$ alkoxy;
Y is selected from the group consisting of:
(1) —O—, and
(2) —$N(R^9)$—, wherein $R^9$ is as defined above.

3. The compound of claim 1 wherein $R^2$ is $C_{1-6}$ alkyl, unsubstituted or substituted with one or more of the substituents selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$NR^9R^{10}$, wherein $R^9$ and $R^{10}$ are independently selected from:
    (i) hydrogen,
    (ii) phenyl,
    (iii) $C_{1-6}$ alkyl, unsubstituted or substituted with one or more of the substituents selected from:
      (A) hydroxy,
      (B) oxo,
      (C) $C_{1-6}$ alkoxy,
      (D) phenyl-$C_{1-3}$ alkoxy,
      (E) phenyl,
      (F) —CN,
      (G) halo,
      (H) —$NR^{14}R^{15}$, wherein $R^{14}$ and $R^{15}$ are independently selected from hydrogen, $C_{1-6}$ alkyl, phenyl, and-$CO_2$-$C_{1-6}$ alkyl,
      (I) heteroaryl, wherein heteroaryl is selected from the group consisting of:
        (a) furanyl,
        (b) pyrrolyl,
        (c) pyridyl,
        (d) imidazolyl,
        (e) oxadiazolyl,
        (f) pyrazolyl,
        (g) triazolo,
        (h) tetrazolo,
        (i) pyrimidyl,
        (j) oxazolo,
        (k) isooxazolo,
        (l) thiazolo, and
        (m) thiadiazolo, and wherein the heteroaryl is unsubstituted or substituted with one or more substituent(s) selected from:
          (I) $C_{1-6}$ alkyl,
          (II) $C_{1-6}$ alkoxy,
          (III) —$NR^{14}R^{15}$, wherein $R^{14}$ and $R^{15}$ are as defined above,
          (IV) halo, and
          (V) trifluoromethyl;
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$NR^{14}CONR^9R^{10}$, wherein $R^9$, $R^{10}$ and $R^{14}$ are as defined above,
(l) —$CONR^9R^{10}$, wherein $R^9$ and $R^{10}$ are as defined above,
(m) —$COR^9$, wherein $R^9$ is as defined above,
(n) —$CO_2R^9$, wherein $R^9$ is as defined above,
(o) —$S(O)_n$-$R^9$, wherein n is 0, 1 or 2 and $R^9$ is as defined above.

4. The compound of claim 1 wherein $R^2$ is $C_{1-6}$ alkyl, unsubstituted or substituted with one or more of the substituents selected from:
  (A) —$NR^{14}R^{15}$, wherein $R^{14}$ and $R^{15}$ are independently selected from hydrogen, $C_{1-6}$ alkyl, and phenyl,
  (B) heteroaryl, wherein heteroaryl is selected from the group consisting of:
    (a) furanyl,
    (b) pyrrolyl,
    (c) pyridyl,
    (d) imidazolyl,
    (e) oxadiazolyl,
    (f) pyrazolyl,
    (g) triazolo,
    (h) tetrazolo,
    (i) pyrimidyl,
    (j) oxazolo,
    (k) isooxazolo,
    (l) thiazolo, and
    (m) thiadiazolo, and wherein the heteroaryl is unsubstituted or substituted with one or more substituent(s) selected from:
      (i) $C_{1-6}$ alkyl,
      (II) $C_{1-6}$ alkoxy,
      (III) —$NR^{14}R^{15}$, wherein $R^{14}$ and $R^{15}$ are as defined above,
      (IV) halo, and
      (V) trifluoromethyl.

5. The compound of claim 1 wherein Y is —O—.

6. The compound of claim 1 wherein Y is selected from the group consisting of:
(1) —$N(R^9)$—,
(2) —$N(COR^9)$—,
(3) —$N(CO^2R^9)$—, and
(4) —$N(CONR^9R^{10})$—, wherein $R^9$ and $R^{10}$ are as defined in claim 1.

7. A compound which is selected from the group consisting of:
1) 3-(SR)-(3,5-bis(trifluoromethyl)benzyloxy)-2-(SR)-phenyl-1-(SR)-cyclohexylacetamide;

2) 3-(SR)-(3,5-bis(trifluoromethyl)benzyloxy)-2-(SR)-phenyl-1-(SR)-cyclohexylacetic acid, 3-(aminomethyl)-pyridine carboxamide;

3) 3-(SR)-(3,5-bis(trifluoromethyl)benzyloxy)-2-(SR)-phenyl-1-(SR)-cyclohexylacetic acid, 4-(aminomethyl)pyridine carboxamide;

4) α-aminocarbonylamino-3-(SR)-(3,5-bis(trifluoromethyl)-benzyloxy)-2-(SR)-phenyl-1-(SR)-methyl-cyclohexane; and 5) α-3-(pyridylmethyl)aminocarbonylamino-3-(SR)-(3,5-bis(trifluoromethyl)benzyloxy)-2-(SR)-phenyl-1-(SR)-methylcyclohexane;

or a pharmaceutically acceptable salt thereof.

8. A pharmaceutical composition comprising a pharmaceutically acceptable carrier and an efective amount of the compound of claim 1.

* * * * *